United States Patent [19]

Marchbanks

[11] Patent Number: 4,841,986
[45] Date of Patent: Jun. 27, 1989

[54] METHOD AND APPARATUS FOR MEASURING INTRACRANIAL FLUID PRESSURE

[76] Inventor: Robert J. Marchbanks, 19, Middle Road, Lymington, Hampshire SO41 9 HE, United Kingdom

[21] Appl. No.: 99,438

[22] Filed: Sep. 17, 1987

[30] Foreign Application Priority Data

Sep. 19, 1986 [GB] United Kingdom ............... 8622671

[51] Int. Cl.$^4$ ............................................. A61B 5/12
[52] U.S. Cl. ................................... 128/746; 128/748
[58] Field of Search .................... 128/748, 746, 774

[56] References Cited

U.S. PATENT DOCUMENTS

| | | | |
|---|---|---|---|
| 3,716,046 | 2/1973 | Janeke | 128/746 |
| 3,949,735 | 4/1976 | Klar et al. | 128/746 |
| 4,002,161 | 1/1977 | Klar et al. | 128/746 |
| 4,079,198 | 3/1978 | Bennett | 128/746 |
| 4,289,143 | 9/1981 | Canavesio et al. | 128/746 |
| 4,413,634 | 11/1983 | Marchbanks | 128/746 |
| 4,429,702 | 2/1984 | Von Recklinghausen | 128/746 |
| 4,459,996 | 7/1984 | Teele | 128/746 |
| 4,462,411 | 1/1984 | Rickards | 128/746 |
| 4,546,779 | 10/1985 | Meno | 128/746 |

FOREIGN PATENT DOCUMENTS

| | | |
|---|---|---|
| 1522031 | 8/1978 | United Kingdom . |
| 2060881 | 5/1981 | United Kingdom . |
| WO79/00614 | 9/1979 | World Int. Prop. O. . |

OTHER PUBLICATIONS

"A New Method for Noninvasive Measurement of Short-Term Cerebrospinal Fluid Pressure Changes in Humans", *Journal of Neurology*, by Richard Kast, Spring 1985, pp. 260–261.

*Primary Examiner*—Kyle L. Howell
*Assistant Examiner*—Angela D. Sykes
*Attorney, Agent, or Firm*—Young & Thompson

[57] ABSTRACT

Intracranial fluid pressure is measured as a function of a characteristic or characteristics of an eardrum. Either or both of the displacement of the eardrum when the stapedius muscle is stimulated or the aural acoustic compliance of the eardrum is measured and provided the cochlear aqueduct is open this will give an indication of intracranial fluid pressure without surgery. Acoustic compliance is measured under conditions of tympanometry but the tympanometry facility is disabled during displacement measurement. The data obtained by the method of the invention may be compared with reference data obtained from the same patient or in clinical trials to provide a real-time record of intracranial fluid pressure changes. Preferably eardrum displacement is used as a baseline measure and acoustic compliance measurement records short-term variation, the two records being combined by computer. Reference data may be input to the computer to update the information displayed. This reference data may include known variations determined by surgery or caused by a postural manoeuvre of the patient.

16 Claims, 3 Drawing Sheets

METHOD AND APPARATUS FOR MEASURING INTRACRANIAL FLUID PRESSURE

FIELD OF THE INVENTION

This invention relates to a method of measuring intracranial fluid pressure and to apparatus for carrying out the method.

BACKGROUND OF THE INVENTION

Conventional intracranial pressure monitoring involves, to a large extent, surgery with inevitable patient morbidity. Lumbar puncture is the most common medical procedure for the indirect assessment of intracranial pressure. This technique is, however, performed by trained medical personnel and is not especially suitable for serial pressure monitoring. Serial pressure monitoring is normally undertaken by surgically making a borehole through the cranium and inserting a tap which is connected to a pressure transducer and recording equipment. The period of time during which such a monitor may remain in place is often severely limited due to the risk of infection and tissue rejection. Because of the associated patient morbidity, risk of infection and the need for professional medical personnel this technique is often not used on patients who might otherwise benefit from pressure monitoring.

OBJECTS OF THE INVENTION

A principal object of the invention is to obviate the limitations of known procedures for intracranial pressure monitoring and to provide a technique, and apparatus for carrying it out, which obviates surgery and thus the need for surgeons and surgical facilities.

Another object of the invention is to provide a technique, and apparatus for carrying it out, which may be used intermittently over long periods of time on patients who otherwise could not be tested for medical or ethical reasons, and which will involve considerably less danger and discomfort for the patient.

SUMMARY OF THE INVENTION

In accordance with one aspect of the invention there is provided a method of measuring intracranial fluid pressure which comprises measuring the movement of an eardrum in response to the stimulation of stapedial muscle contraction.

The said measurement may be compared with reference data obtained by another method of measuring intracranial fluid pressure.

Preferably the method additionally comprises measuring the acoustic compliance of the eardrum.

The successful monitoring of intracranial fluid pressure by measuring movement of an eardrum in response to stapedial muscle contraction does require that changes in intracranial fluid pressure are transmitted to the fluid within the inner ear of at least one ear of the patient under test. In general this requires the cochlear aqueduct to be open. However this condition is satisfied in the majority of people.

Changes in the inner ear fluid pressure in turn alter certain mechanical and acoustical properties of the ear. Preferably the perturbations in the mechanical properties of the inner ear are serially measured with time in terms of movements of the ear drum induced by contraction of the stapedial muscle. The said movements may be quantified in a direct manner as displacement using volume flow measurement apparatus. An example of suitable apparatus is to be found in U.S. Pat. No. 4,413,634. This discloses apparatus capable of measuring movement of the ear drum in terms of a volume displacement. Alternatively the said movements may be quantified in an indirect manner using extratympanic manometry, or any other known suitable measurement apparatus may be employed.

Measurement of changes in intracranial pressure in terms of ear drum movement alone will provide a sensitive indirect measure with long-term stability, but it will have four main disadvantages. Firstly, the ear drum movement is measured as a complex waveform which in its raw state is unsuitable as a serial measure of fluctuations in intracranial pressure. Secondly, ear drum movement is not in itself a quantitative measure of intracranial pressure and fluctuations thereof. Thirdly the movement measurement will lack temporal resolution, which for example is required in resolving short-term intracranial pressure waves found in a medical condition known as normal hydrocephalus. Fourthly inaccuracies of measurement will occur due to the effects of middle ear pressure.

Therefore it is preferred, in accordance with the invention, that induced ear drum movements are analysed and quantified in terms of one or more parameters which are related to predetermined measures of intracranial pressure. It is further preferred that a rapid switching between measurements of ear drum displacement and of aural acoustic compliance occurs. By means of this compound measurement method the advantages of displacement measurement (precision and long term stability) are combined with the good temporal resolution provided by aural acoustic compliance measurement.

In another aspect the present invention provides a method of serially monitoring intracranial fluid pressure which comprises alternately measuring the movement of an ear drum in response to induced stapedial muscle contracton and the acoustic compliance of said eardrum when pressure on opposite sides thereof is equalised by tympanometry.

The method of the invention may be used before and after a procedure known to induce a predetermined intracranial fluid pressure variation, such as a controlled postural manoeuvre of the subject, and the known data may be combined with the measurement data as a reference parameter.

The said measurements may be compared with reference data obtained by another method of intracranial fluid pressure measurement.

In accordance with yet another aspect of the present invention there is provided apparatus for intracranial pressure monitoring comprising means for the ipsilateral acoustic stimulation of a stapedial muscle, means for measuring the responsive movement of the associated ear drum, means for comparing said measurement with pre-established reference data derived from the measurement of intracranial fluid pressure by other means and read-out means to display the results of said comparison.

The apparatus may further comprise tympanometry means, means for measuring the aural acoustic compliance of said ear drum while the latter is under the influence of the tympanometry means and transducer means for converting the acoustic wave reflected from said eardrum into an electrical signal.

Means may be provided for alternately actuating the eardrum movement measurement and the acoustic compliance measurement means and for disabling the tympanometry means when the eardrum displacement measurement means is actuated. Means is preferably provided for combining electrical signals produced by the two measurement means so that aural acoustic compliance may be calibrated in terms of ear drum displacement.

The apparatus may further comprise means for combining with said signals an electrical signal derived from intracranial fluid pressure measurements effected separately and displaying a record of the combined data.

In accordance with yet another aspect of the invention there is provided apparatus for serially monitoring intracranial fluid pressure comprising tympanometry means, means for measuring the acoustic compliance of an eardrum while under the influence of said tympanometry means, means for disabling the tympanometry means, means for stimulating the stapedial muscle associated with said eardrum and for measuring the responsive displacement of said eardrum and means for actuating said measurement means alternately with said tympanometry means disabled during measurement of eardrum displacement.

BRIEF DESCRIPTION OF THE DRAWINGS

The following description of one embodiment of the invention is given by way of non-limitative example.

In the accompanying diagrammatic drawings.

DESCRIPTION OF THE PREFERRED EMBODIMENT

Figure 1:
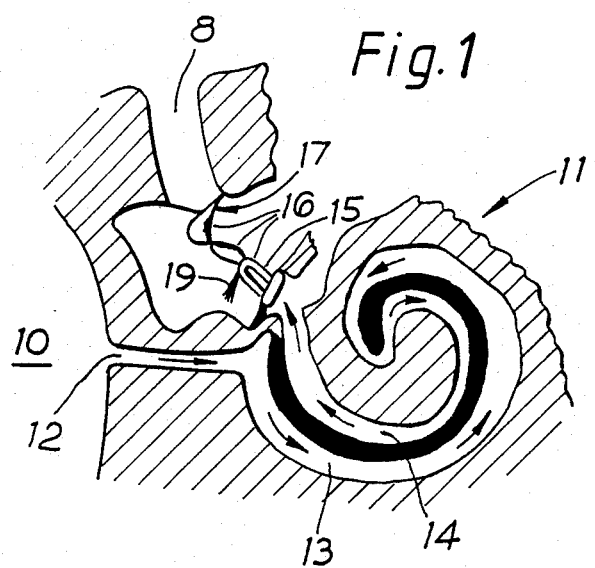
FIG. 1 is a sectional view illustrating the route by which a change in the intracranial fluid pressure is transmitted to the fluid of the inner ear.

FIG. 1 illustrates the functional relationship between the subarachnoid space 10 which contains intracranial fluid and the inner ear generally indicated at 11. A pressure change of the intracranial fluid is transmitted via an open cochlear aqueduct 12 to the perilymphatic fluid within the tympanic scala 13. This induced pressure change is then transmitted to the perilymph of the vestibular scala 14 and onto the stapes 15 which provides the interface between the inner ear 1 and the ossicles 16 and the eardrum 17. It will be apparant that a change in intracranial pressure will affect both the mechanical input compliance of the inner ear 11, and therefore the acoustic compliance of the eardrum 17 and the resting position of the stapes 15 and therefore the mechanics of the ear.

Figure 2:
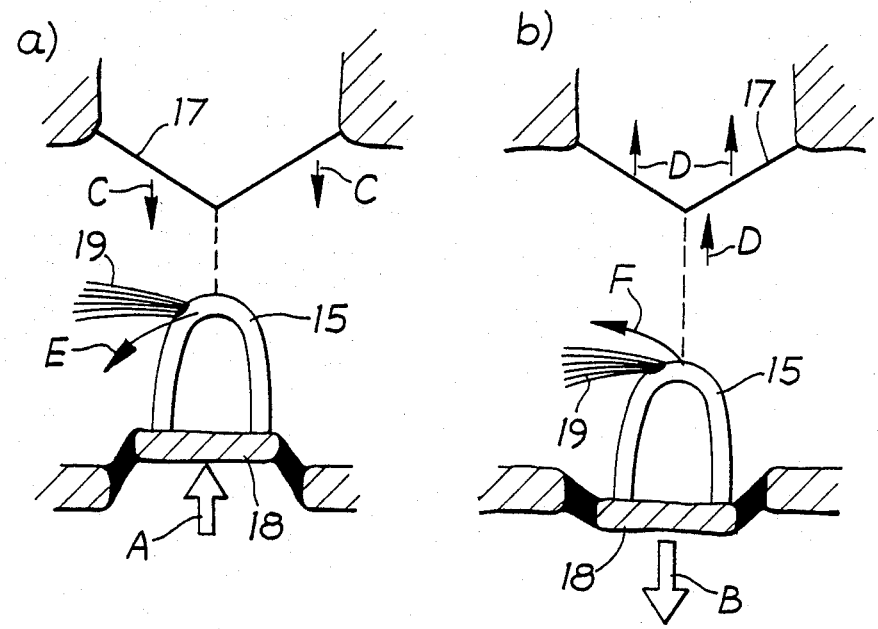
FIGS. 2a and 2b are simplified illustrations of how intracranial pressure influences the mechanics of the stapes, and consequently ear drum motion, FIG. 3 diagrammatically illustrates apparatus in accordance with the present invention.

FIGS. 2a and 2b show how intracranial pressure affects the mechanics of the ear. FIG. 2a illustrates a case of extremely high intracranial fluid pressure. The induced increase in perilymphatic pressure indicated by arrow A causes the base 18 of the stapes 15 to rest at a position displaced out toward the eardrum 17. Contraction of the stapedial muscle 19, such as brought about by acoustic stimulation, causes the base 18 of the stapes to rotate about its anterior region which in turn causes a corresponding inward movement of the eardrum 17 as indicated by the arrows C. Conversely, and as illustrated in FIG. 2b, if intracranial pressure is extremely low the base 18 of the stapes will be displaced inwardly in the direction of arrow B away from the eardrum 17. Contraction of the stapedial muscle 19 will cause outward rotation of the stapes 15 and a corresponding outward movement of the eardrum 17 as indicated by the arrows D. The direction of movement of the head of the stapes 15 is indicated by the arrow E in FIG. 2a and F in FIG. 2b.

Thus it will be seen that changes in the intracranial pressure are transmitted to the perilymphatic fluid of the inner ear 11. Variations in this aural fluid pressure in turn alter the mechanics of the stapes 15, this being the innermost ossicle of the middle ear coupled to the perilymph by means of the oval window. These changes in stapes mechanics can be measured in terms of movement of the eardrum in response to stapedial muscle contraction. Provided the cochlear aqueduct 12 is open an increase in intracranial fluid pressure will cause a more inward movement of the eardrum 17 and a decrease will cause a more outward movement. The method of the present invention proceeds from a realisation that since the fluctuations in the intracranial pressure are related to changes in the characteristics of the eardrum (position and/or acoustic compliance) an indirect measure of intracranial fluid pressure may be obtained by measuring these characteristics of the inner ear.

Figure 3:
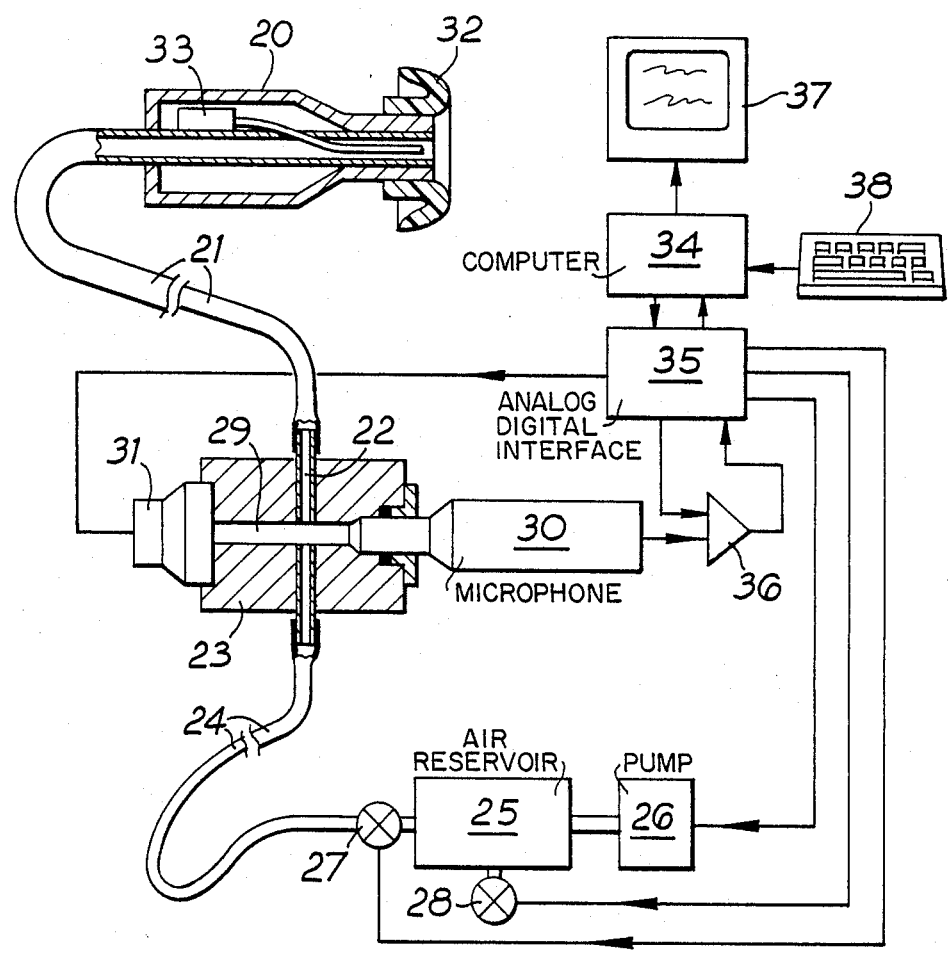

FIG. 3 illustrates apparatus for carrying out the method of the invention in which an aural probe 20 is connected by a flexible tube 21 to one end of a cross-bore 22 in a block 23. The other end of the cross-bore 22 is connected by a flexible tube 24 to an air reservoir 25 fed by a pump 26. The reservoir 25 can be isolated from the tube 24, and thus the probe 20, by a solenoid-operated valve 27 and vented to atmosphere through another solenoid-operated valve 28.

The cross-bore 22 intersects and communicates with a main bore 29 in the block 23. At one end of the main bore 29 is a pressure transducer in the form of a microphone 30 of a kind known as "D.C.", i.e. having a response which extends from audio frequencies down to infrasonics. At the opposite end of the main bore 29 is a servo-controlled reference diaphragm 31, the function of which is to compensate for pressure variations produced by the eardrum 17 and thus allow eardrum displacement measurement to be facilitated since the volume displacement of the reference diaphragm is a known function of its input voltage. Reference is made to U.S. Pat. No. 4,413,634 for a fuller understanding of the components of the apparatus so far described.

At its end remote from the tube 21 the probe 20 has a resilient cup 32 to make an air seal with the ear under test, and inbuilt into the probe 20 is a miniature loudspeaker 33 of the kind used in hearing aids. In this embodiment of the invention the loudspeaker 33 is used both for the ipsilateral acoustic stimulation which will enable responsive eardrum displacement to be measured and for generating the sound wave the reflection of which will be used to measure aural acoustic compliance.

A digital computer 34 is arranged to receive, process and record eardrum movement and aural compliance signals from an analogue-digital interface 35. This receives signals from the microphone 30 through a summing amplifier 36 which is balanced by digital servo control signals made by the computer through the interface 35 to remove the quiescent voltage produced by the air pressure currently prevailing in the tubes 21 and 24. By this means the eardrum displacement measurements will be unaffected by the said air pressure. The computer 34 also serves for the automatic determination of middle ear pressure by tympanometric means and control of the air pump 26 and sequencing of the valves 27 and 28 such that during acoustic compliance and eardrum displacement measurements pressure on opposite sides of the eardrum under test is equalised and such that during eardrum displacement measurement the probe 20 is isolated from the air reservoir 25 by closure of the valve 27. This ensures that the total enclosed volume is kept to a minimum as required by low volume flow measurement and furthermore that microphone 30 is isolated from inherent noise of the pump 26.

Patient and test information can be input to the computer 34 by a keyboard 38 and the computer displays its analysis of the input information in the form of intracranial fluid pressure traces on a visual display unit 37.

In use of the apparatus of FIG. 3, the cup 32 makes an air seal with the patient's ear, whereupon the computer 34 effects tympanometry, i.e. it senses middle ear pressure and balances it with an equal pressure in the outer ear canal by suitable operation of the air pump 26. At predetermined intervals the loudspeaker 33 is caused to emit a sound wave which provides an acoustic stimulus of an intensity sufficient to cause contraction of the stapedial muscle. During one such emission motion of the eardrum as a result of subsequent contraction of the stapedial muscle is measured in terms of volume displacement by combined action of the microphone 30 acting as a pressure-sensitive transducer and servo control of the reference diaphragm 31 to compensate for pressure changes resulting from eardrum displacement. During this emission the function of tympanometry is disabled by the computer 34 and closure of the valve 27 occurs. During a subsequent emission of an intensity below that sufficient to cause contraction of the stapedial muscle the valve 27 is opened and the computer 34 carries out the function of tympanometry. The sound wave reflected from the eardrum under this test condition is converted by the microphone 30 into an electrical signal provided to the computer 34. Recordings of perturbations in the aural acoustic compliance due to fluctuations in the intracranial pressure are stored within the computer 34 and made continuously except during periods of rapid switching to ear drum movement measurement. A running ensemble average of nominally 20 records of ear drum movement are made at a frequency of nominally 2 records per minute. The ensemble averaged waveforms are digitally analysed and expressed in terms of one or more parameters which have a predetermined relationship with absolute intracranial pressure as obtained from prior clinical trials on a large subject population. These parameters may be built in to the computer 34 or input by the keyboard 38. After subtracting the measured middle ear pressure to yield an estimate of the absolute baseline intracranial pressure, running values of intracranial pressure and standard errors obtained by this method are displayed in real time as a serial trace by the visual display unit 37. In a similar manner the corresponding ongoing recording of short-term intracranial pressure fluctuations made using the acoustic compliance measurements are displayed with the exception of high-pass filtering with a time constant of nominally 5 minutes to remove base-line drift. Signal noise allowing, serial compliance measures may be correlated with serial eardrum movement measures in overlapping spectral bands and this allows compliance to be calibrated in terms of eardrum movement and therefore in terms of intracranial pressure. The two serial measurements can be mathematically combined by the computer 34 using standard spectral analysis methods to provide a single wide bandwidth intracranial pressure recording.

At any time the eardrum movement may be precisely calibrated in terms of relative or absolute intracranial pressure if measurements of the said movement have been made during known changes in the relative or absolute value of intracranial pressure. An example of this is the pressure change known to result from a controlled postural manouvre of the patient. Such information may be input to the computer 34 by the keyboard 38 and the pressure scales on the serial pressure display will immediately be updated accordingly. In practice such calibration may be achieved by recording eardrum movement under various conditions, for example during periods of known intracranial pressure normality, during periods of direct intracranial pressure measurement by surgical procedure or during a controlled manoeuvre of the subject's posture which provides a standardised and approximately known change in intracranial pressure.

Figure 4:
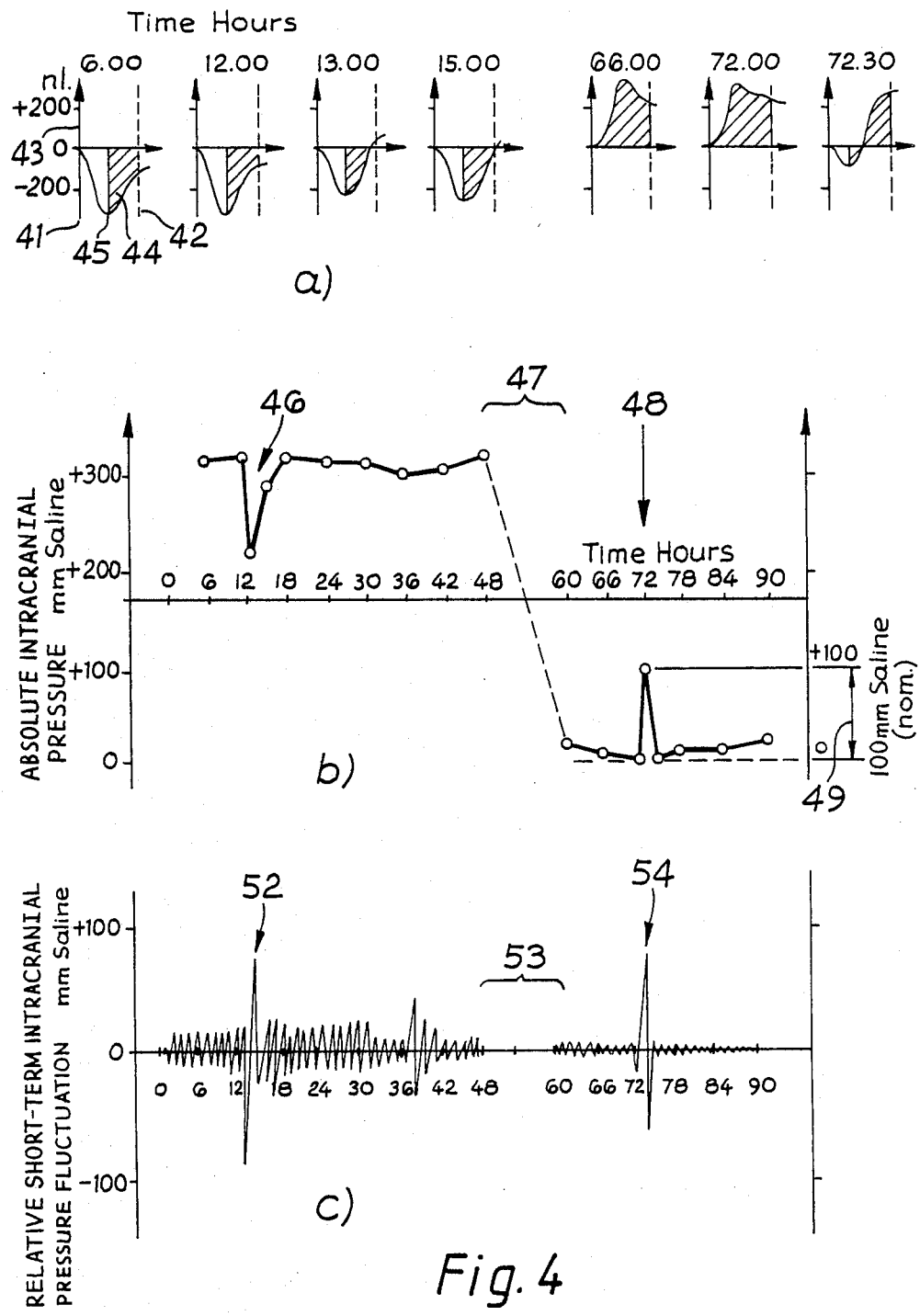
FIG. 4a illustrates the conversion of a trace of ear drum displacements into a stable baseline pressure record.
FIG. 4b is a record of changes in the baseline intracranial pressure over a monitored 90 hour period.
FIG. 4c illustrates the corresponding short-term intracranial pressure fluctuations.

The serial traces exemplified in FIG. 4 will now be explained. The seven graphs shown in FIG. 4a record movement of the eardrum and changes in the pattern of this movement for variations in the intracranial pressure. Measurements of ear drum motion for various times after the patient's admission, 0 hour, are shown. Measurements at times 6.00, 15.00, 72.00 and 72.30 hours are real data from a patient with benign intracranial hypertension, which is a medical condition of raised intracranial fluid pressure. The remaining data of FIG. 4a is included for the sake of simplicity without standard errors. Also for the sake of clarity recordings of baseline and short-term intracranial pressure fluctuations have not been mathematically combined as previously described.

The recorded eardrum movements result from contraction of the stapedius muscle brought about by a 1000 Hertz, 115 dB SPL acoustic stimulus, i.e. ipsilateral stimulation. The stimulus was of 500 ms duration and the graphs show ear drum motion from the time of stimulus switch-on indicated at 41 to the time of switch-off indicated at 42. Each graph represents an ensemble average of the eardrum motion for 15 repeats of this stimulus. The movement of the eardrum is expressed on the vertical axis 43 as a volume displacement measured in nanolitres (nl). A positive displacement value corresponds to an outward movement of the eardrum and a negative displacement value to an inward movement. Intracranial pressure has been quantified at the various times shown in terms of the mean displacement 44 of the eardrum (Vm) measured from the instant 45 of maximum inward displacement to the instant 42 of switch-off of the stimulus. These mean displacements (Vm) are derived using a computer algorithm and their values are initially transformed to provide a recording of the intracranial pressure as shown in FIG. 4b, using predetermined relationships obtained during prior clinical trials on a large subject population. FIG. 4b shows various changes in the base-line intracranial pressure over the monitored 90 hour period. FIG. 4c illustrates the corresponding short-term intracranial pressure fluctuations measured by the acoustic compliance means and calibrated in terms in said pressure by first calibrating in terms of eardrum displacement as previously described.

An exploratory lumbar-puncture was undertaken on this patient to confirm the medical diagnosis of raised intracranial fluid pressure and FIGS. 4b and 4c show the resulting pressure change at 46 and 52, respectively. At this time an estimate of the absolute intracranial pressure was obtained as 350 mm saline and the present invention allows this to be entered by means of the keyboard 38 with the result that the absolute pressure scale of FIG. 4b is realigned. After 48 hours a lumbar-shunt was surgically inserted into the patient and this successfully reduced the intracranial pressure to within normal limits as indicated at 47 and 53. After 72 hours the measurement method was finally calibrated using an actual controlled change in pressure indicated at 48 and 54, brought about by a postural manoevre of the patient known to bring about an increase in pressure by nominally 100 mm saline as indicated at 49 in FIG. 4b. Again the estimate of pressure change was entered by means of the keyboard 38 and this facilitated final adjustment of both the absolute and relative intracranial pressure scales for both the base line of FIG. 4b and the short-term fluctuations of FIG. 4c.

It will be appreciated that although the present invention is directed to a non-surgical technique and apparatus for carrying it out minor surgical procedures may be necessary under certain conditions. As well as serial monitoring a single assessment of the state of the intracranial pressure with or without calibration against known or standardised data is within the scope of the invention.

What is claimed is:

1. A method of serially monitoring the intracranial fluid pressure of a subject which comprises alternately obtaining measurements related to the magnitude and direction of the volume displacement of an ear drum in response to induced stapedial muscle contraction and the acoustic compliance of said eardrum when pressure on opposite sides thereof is equalised by tympanometry, and using said measurements serially to monitor the intracranial fluid pressure of the subject.

2. A method as claimed in claim 1, and comprising converting said measurements into electrical signals, and combining said electrical signals so that one of said measurements may be calibrated in terms of the other.

3. A method as claimed in claim 1, and comprising converting said measurements into electrical signals, combining said electrical signals into a single record and displaying a record of the combined data.

4. A method as claimed in claim 1, wherein the subject is made to undergo a controlled postural manoeuvre between two occasions of monitoring intracranial pressure and the known effects of said manoeuvre on intracranial fluid pressure are included in data with which said measurements are compared.

5. A method as claimed in claim 1 wherein said measurements are compared with reference data obtained by another method of intracranial fluid pressure measurement.

6. Apparatus for serially monitoring intracranial pressure comprising means for the acoustic stimulation of a stapedial muscle, means for obtaining a measurement related to the magnitude and direction of the responsive volume displacement of the associated ear drum, means for comparing said measurement with pre-established reference data derived from the measurement of intracranial fluid pressure by other means and read-out means to display the results of said comparison.

7. Apparatus as claimed in claim 6 and further comprising tympanometry means, means for obtaining a measurement related to the aural acoustic compliance of said ear drum while the latter is under the influence of the tympanometry means and transducer means for converting the acoustic wave reflected from said ear drum into an electrical signal.

8. Apparatus as claimed in claim 7, and comprising means for alternately actuating said means for obtaining a measurement related to the ear drum displacement and said means for obtaining a measurement related to the aural acoustic compliance and for disabling the tympanometry means when the means for obtaining a measurement related to the ear drum displacement is actuated.

9. Apparatus for serially monitoring intracranial fluid pressure comprising tympanometry means, means for obtaining a measurement related to the acoustic compliance of an ear drum while under the influence of said tympanometry means, means for disabling the tympanometry means, means for stimulating contraction of the stapedial muscle associated with said ear drum and for obtaining a measurement related to the magnitude and direction of the responsive volume displacement of said ear drum, means for actuating said measurement means alternately with said tympanometry means and means for obtaining a measurement related to the acoustic compliance disabled when obtaining a measurement related to said ear drum displacement, and means for using said measurement related to the magnitude and direction of the responsive volume displacement of said ear drum to monitor intracranial fluid pressure.

10. Apparatus as claimed in claim 9 and comprising means for combining electrical signals produced by the two measurement means so that one of said measurements may be calibrated in terms of the other.

11. Apparatus as claimed in claim 10, and further comprising means for combining said electrical signals into a single record and displaying a record of the combined data.

12. A method of serially monitoring the intracranial fluid pressure of a subject, which comprises providing measuring means for obtaining a measurement related to the magnitude and direction of volume displacement of an ear drum, generating and applying to an ear drum an acoustic signal sufficient to stimulate contraction of the stapedial muscle, operating said measuring means to obtain a measurement related to the magnitude and direction of volume displacement of the ear drum in response to said stapedial muscle contraction, and using said measurement to monitor the intracranial fluid pressure of the subject.

13. A method as claimed in claim 12, wherein the said measurement is compared with reference data obtained by another method of measuring intracranial fluid pressure.

14. A method as claimed in claim 12 and additionally comprising measuring the acoustic compliance of the eardrum.

15. A method as claimed in claim 12 which comprises obtaining said measurement before and after a procedure known to induce a predetermined intracranial fluid pressure variation.

16. A method as claimed in claim 15 wherein the said procedure is a controlled postural manoeuvre of the subject.

* * * * *